(12) United States Patent
Bukawa et al.

(10) Patent No.: US 9,226,888 B2
(45) Date of Patent: Jan. 5, 2016

(54) COMPOSITIONS CONTAINING AN ACRYLIC FILM FORMER, A TACKIFIER AND AN ESTER

(75) Inventors: Yoriko Bukawa, Chuou-ku (JP); Hy Si Bui, Piscataway, NJ (US); Momoko Shimizu, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/354,719

(22) PCT Filed: Dec. 30, 2011

(86) PCT No.: PCT/US2011/068059
§ 371 (c)(1),
(2), (4) Date: Apr. 28, 2014

(87) PCT Pub. No.: WO2013/101171
PCT Pub. Date: Jul. 4, 2013

(65) Prior Publication Data
US 2014/0242014 A1    Aug. 28, 2014

(51) Int. Cl.
| | |
|---|---|
| A61K 8/81 | (2006.01) |
| A61K 8/85 | (2006.01) |
| A61K 8/02 | (2006.01) |
| A61K 8/37 | (2006.01) |
| A61Q 1/02 | (2006.01) |
| C08K 5/10 | (2006.01) |
| C09D 133/02 | (2006.01) |
| A61Q 1/06 | (2006.01) |

(52) U.S. Cl.
CPC ............. *A61K 8/8152* (2013.01); *A61K 8/0229* (2013.01); *A61K 8/37* (2013.01); *A61K 8/8117* (2013.01); *A61K 8/85* (2013.01); *A61Q 1/02* (2013.01); *A61Q 1/06* (2013.01); *C09D 133/02* (2013.01); *A61K 2800/31* (2013.01); *A61K 2800/594* (2013.01); *C08K 5/10* (2013.01)

(58) Field of Classification Search
None
See application file for complete search history.

(56) References Cited

U.S. PATENT DOCUMENTS

| | | | |
|---|---|---|---|
| 7,875,265 | B2 | 1/2011 | Blin et al. |
| 8,119,110 | B2 | 2/2012 | Blin et al. |
| 8,586,013 | B2 | 11/2013 | Bradshaw et al. |
| 2004/0191279 | A1 | 9/2004 | Klofta |
| 2006/0093568 | A1 | 5/2006 | Blin et al. |
| 2006/0115444 | A1 | 6/2006 | Blin et al. |
| 2006/0147402 | A1 | 7/2006 | Blin et al. |
| 2007/0134181 | A1 | 6/2007 | Shimizu et al. |
| 2007/0190001 | A1 | 8/2007 | Jacques et al. |
| 2008/0025934 | A1 | 1/2008 | Lebre et al. |
| 2009/0130037 | A1 | 5/2009 | Thevenet et al. |
| 2010/0310489 | A1 | 12/2010 | Barba |
| 2011/0020263 | A1 | 1/2011 | Ilekti et al. |
| 2011/0280817 | A1 | 11/2011 | Ramadan et al. |
| 2012/0171139 | A1 | 7/2012 | Bradshaw et al. |
| 2013/0171084 | A1 | 7/2013 | Kawaratani et al. |

FOREIGN PATENT DOCUMENTS

| | | | |
|---|---|---|---|
| CN | 101897655 A | * | 12/2010 |
| JP | 2007-269746 | | 10/2007 |

OTHER PUBLICATIONS

U.S. Appl. No. 14/359,791, filed May 21, 2014, Bui, et al.
U.S. Appl. No. 14/363,215, filed Jun. 5, 2014, Bukawa, et al.
International Search Report issued Sep. 20, 2012, in PCT/US11/068059 filed Dec. 30, 2011.

* cited by examiner

*Primary Examiner* — David J Blanchard
*Assistant Examiner* — Sarah Chickos
(74) *Attorney, Agent, or Firm* — Oblon, McClelland, Maier & Neustadt, L.L.P.

(57) ABSTRACT

The invention relates to a composition, especially a cosmetic composition, comprising at least one ester of polyol(s) and of fatty diacid dimer or an ester thereof, at least one acrylic film forming agent and at least one tackifier, as well as to methods of using such compositions.

14 Claims, No Drawings

COMPOSITIONS CONTAINING AN ACRYLIC FILM FORMER, A TACKIFIER AND AN ESTER

FIELD OF THE INVENTION

The present invention relates to compositions comprising at least one ester of polyol(s) and of fatty diacid dimer or an ester thereof, at least one at least one acrylic film forming agent and at least one tackifier. Among other improved or beneficial properties, these compositions have surprisingly good stability, shine, wear, transfer-resistance, texture, and feel upon application properties.

DISCUSSION OF THE BACKGROUND

Many cosmetic compositions, including pigmented cosmetics such as foundations and lipsticks, have been formulated in an attempt to posses long wearing properties upon application. Unfortunately, many of these compositions do not generally possess both good long-wear/transfer-resistance properties and good application properties.

For example, commercial products containing silicon resins such as MQ resins are known. Such products are known to provide good long wear properties and/or transfer-resistance. However, such compositions possess poor application properties and poor feel upon application (owing to the film formed by the MQ resin).

Thus, there remains a need for improved cosmetic compositions having improved cosmetic properties, particularly good wear, feel, and texture characteristics upon application.

Accordingly, one aspect of the present invention is a care and/or makeup and/or treatment composition for keratinous materials which has good cosmetic properties such as, for example, good shine, feel, wear and/or texture properties upon application.

SUMMARY OF THE INVENTION

The present invention relates to compositions comprising at least one ester of polyol(s) and of fatty diacid dimer or an ester thereof, at least one at least one acrylic film forming agent and at least one tackifier. Preferably, the compositions are anhydrous and in the form of a stick.

The present invention also relates to colored compositions comprising at least one coloring agent, at least one ester of polyol(s) and of fatty diacid dimer or an ester thereof, at least one at least one acrylic film forming agent and at least one tackifier. Such colored compositions can be, for example, cosmetic compositions such as lip compositions (for example, lipstick) or foundations. Preferably, the compositions are anhydrous and in the form of a stick.

The present invention also relates to methods of treating, caring for and/or making up keratinous material (for example, skin or lips) by applying compositions of the present invention to the keratinous material in an amount sufficient to treat, care for and/or make up the keratinous material.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, increased shine, increased anti-smudging properties, increased long wear properties, and/or better texture, and/or feel upon application. Preferably, the compositions are anhydrous and in the form of a stick.

The present invention also relates to methods of improving the shine, feel, and/or texture properties of a composition upon application to a keratin material comprising adding to a composition (for example, a lip composition) at least one ester of polyol(s) and of fatty diacid dimer or an ester thereof, at least one at least one acrylic film forming agent and at least one tackifier.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to lips followed by rubbing a material, for example, a sheet of paper, against the lips after expiration of a certain amount of time following application, such as 2 minutes after application. Similarly, transfer resistance of a composition may be evaluated by the amount of product transferred from a wearer to any other substrate, such as transfer from the lips of an individual to a collar when putting on clothing after the expiration of a certain amount of time following application of the composition to the lips. The amount of composition transferred to the substrate (e.g., collar, or paper) may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Tackifiers

According to the present invention, compositions comprising at least one tackifier are provided. In accordance with the present invention, a substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant, for example, that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter $\delta$ according to the Hansen solubility space is defined in the article "*Solubility Parameter Values*" by Eric A. Grulke in the work "*Polymer Handbook*" 3$^{rd}$ edition, Chapter VII, pages 519-559, the entire content of which is hereby incorporated by reference, by the relationship:

$$\delta = (d_D^2 + d_P^2 + d_H^2)^{1/2}, \text{ in which:}$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like).

The definition of the solvents in the three-dimensional solubility space according to Hansen is given in the article by C. M. Hansen: "*The three-dimensional solu-* bility parameters" J. Paint Technol., 39, 105(1967), the entire content of which is hereby incorporated by reference.

The at least one tackifier used in the present invention preferably has a solubility parameter corresponding to δ and the block copolymer preferably has at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar, where "non-polar" means that the tackifier is substantially free of monomers having polar groups. Preferably, polar groups are not present; however, if they are present, they are preferably present in an amount of up to about 5% by weight, preferably up to about 2% by weight, and more preferably up to about 0.5% by weight.

In preferred embodiments, the tackifier may have a softening point (Ring and Ball, as measured by ASTM E-28) of about 80° C. to about 150° C., preferably about 100° C. to about 130° C. In other preferred embodiments, the tackifier may be liquid and have an R and B softening point of between about −70° C. and about 70° C.

According to preferred embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred tackifier for use in the present invention is a hydrogenated hydrocarbon resin such as, for example, a hydrogenated styrene/methyl styrene/indene copolymer, commercially available from Eastman under the tradename Regalite® R1100.

In the composition of the present invention, the tackifier(s) are preferably present in an amount of from about 0.1 to about 30 percent by weight, more preferably from 1 to 25 percent by weight, more preferably from 3 to 20 percent by weight and most preferably from 5 to 15 percent by weight of the total weight of the composition, including all ranges and subranges therebetween.

Acrylic Film Forming Agents

According to the present invention, compositions comprising at least one at least one acrylic film forming agent (film former) are provided. Acceptable film forming agents are known in the art and include, but are not limited to, those disclosed in U.S. patent application 2004/0170586 and U.S. patent application 2011/0020263, the entire contents of which are hereby incorporated by reference in their entirety.

"Acrylic film formers" as used herein refers to polymers that are film forming agents and which are based upon one or more (meth)acrylic acid (and corresponding (meth)acrylate) monomers or similar monomers.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, octafluoropentyl acrylate, octafluoropentyl methacrylate, 2,2,2-trifluoroethyl methacrylate, 1,1,1,3,3,3-hexafluoroisopropyl acrylate, 1,1,1,3,3,3-hexafluoroisopropyl methacrylate, 2,2,3,3,3-pentafluoropropyl methacrylate, 2,2,3,4,4,4-hexafluorobutyl methacrylate, 2,2, 3,3,4,4,4-heptafluorobutyl acrylate, 2,2,3,3,4,4,4-heptafluorobutyl methacrylate, 2,2,3,3,4,4,5,5,6,6,7,7,8,8,8-pentadecafluorooctyl methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 13 000 g/mol), poly(methyl methacrylate) ethyl methacrylate (Mw of 2000 to 8000 g/mol).

A particularly preferred film former is a copolymer of acrylic acid, isobutyl acrylate and isobornyl acetate such as that sold under the names Pseudoblock (Chimex) and Synamer-3. In both of these commercial products, the copolymer is present with a solvent in a 1:1 ratio (50% solid). Another preferred film former is Poly(isobornyl methacrylate-8 co-isobornyl acrylate-co-isobutyl acrylate-co-acrylic acid) at 50% of active material in 50% of octyldodecyl neopentanoate, (Mexomere PAZ from Chimex).

According to preferred embodiments, the film former is present in the composition in an amount ranging from 0.1% to 30% by weight relative to the total weight of the composition. Preferably, the film former is present in an amount ranging from 1% to 20% by weight relative to the total weight of the composition, and more preferably from 5% to 15%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to preferred embodiments, the tackifier and the acrylic film forming agent are present in the compositions of the present invention in a weight ratio of between 10:1 and 1:10, preferably between 5:1 and 1:5, and preferably between 2:1 and 1:2, including all ranges and subranges therebetween.

Ester of Polyol(s) and of Fatty Diacid Dimer or an Ester Thereof

According to the present invention, compositions comprising at least one ester of polyol(s) and of fatty diacid dimer or an ester thereof are provided. Suitable examples of at least one ester of polyol(s) and of fatty diacid dimer or an ester thereof can be found in U.S. patent application nos. 2007/0134181, 2007/0134182, 2007/0134192, and 2007/0190001, the entire contents of which are hereby incorporated by reference.

In the phrase "ester of polyol(s) and of fatty diacid dimer, or an ester thereof," the term "or an ester thereof" means one of the derivatives of these esters and of polyol(s) and of fatty diacid dimer obtained either by reaction of alcohol function(s) of the polyol, not engaged in bonds of ester type with acid functions of the diacid dimer, with one or more carboxylic functions of acid molecules other than the diacid dimer, or alternatively by reaction of acid function(s) of the diacid dimer, not engaged in bonds of ester type with alcohol functions of the polyol, with alcohol functions of alcohol molecules other than the polyol.

Preferably, the esters of polyol(s) and of fatty diacid dimer, or an ester thereof, have a viscosity, measured at about 25° C., of greater than or equal to about 1500 mPa·s. For example, the viscosity of an ester of polyol(s) and of fatty diacid dimer, or an ester thereof, suitable for use in the invention may range from about 1500 mPa·s to about 150 000 mPa·s, or for example from about 2000 mPa·s to about 150 000 mPa·s, or for example from about 15 000 mPa·s to about 100 000 mPa·s or for example from about 30 000 mPa·s to about 80 000 mPa·s, including all ranges and subranges therebetween.

Preferably, an ester of polyol(s) and of fatty diacid dimer, or an ester thereof, suitable for use in the present invention may have a molecular weight ranging from about 2000 to about 25 000 g/mol, for example from about 4000 to about 20 000 g/mol, for example from about 5000 to about 20 000 g/mol, for example from about 7000 to about 15 000 g/mol and for example from about 8000 to about 10 000 g/mol, including all ranges and subranges therebetween.

According to preferred embodiments, a polyol that is suitable for use in the invention is a diol dimer. The esters of diol dimer and of fatty diacid dimer that may be used in the context of the present invention are commercially available or may be prepared in a conventional manner. They may be of plant origin and may be obtained by esterification of diacid dimers with diol dimers.

In an esterification reaction with a diacid dimer, a polyol dicarboxylate is obtained. The polyol dicarboxylate preferably has a weight-average molecular weight, determined by gel permeation chromatography (GPC), ranging from 2000 to 25 000 g/mol or for example between 2000 and 4000 g/mol, including all ranges and subranges therebetween.

In an esterification reaction with a diacid dimer, the average degree of esterification and the average molecular weight of the ester obtained may be adjusted by varying the ratio of the diol dimer to the diacid dimer.

Diacid Dimer

According to preferred embodiments of the present invention, the diacid dimer is obtained by a polymerization reaction, for example by intermolecular dimerization, of at least one fatty acid, preferably at least one unsaturated fatty acid. Preferably, the dimer contains at least two carboxylic acid groups.

The carboxylic functions of the diacid dimer not engaged in the ester bond with the polyol residue(s) may be engaged in other ester bonds with other alcohol functions of alcohol molecules other than the polyol(s). These alcohol molecules or residues may be monoalcohols or polyols.

As examples of alcohol residues that are suitable for use in the invention, mention may be made of hydrocarbon-based compounds comprising a hydroxyl function and containing from 4 to 40 carbon atoms, or for example from 6 to 36 carbon atoms, or for example from 8 to 32 carbon atoms, or for example from 16 to 28 carbon atoms, or for example from 18 to 24 carbon atoms.

As examples of monoalcohols that are suitable for the invention, mention may be made, in a non-limiting manner, of butanol, pentanol, propanol, hexanol, heptanol, octanol, decanol, dodecanol, hexadecanol, octadecanol, eicosadecanol, phytosterol, isostearol, stearol, cetol, behenol, etc.

The diacid dimers may be derived for example from the dimerization of an unsaturated fatty acid, for example of $C_8$ to $C_{34}$, or for example of $C_{12}$ to $C_{22}$, in particular of $C_{16}$ to $C_{20}$ and for example of $C_{18}$. As examples of these unsaturated fatty acids, mention may be made for example of undecenoic acid, linderic acid, myristoleic acid, palmitoleic acid, oleic acid, linoleic acid, elaidinic acid, gadolenoic acid, eicosapentaenoic acid, docosahexaenoic acid, erucic acid, brassidic acid and arachidonic acid, and mixtures thereof.

According to certain embodiments of the present invention, the diacid dimer from which the diol dimer is esterified may be in hydrogenated form. The hydrogenated form of the diacid dimer may be partial or total, and may correspond, for example, to the saturated form, which is more stable towards oxidation.

According to a preferred embodiment, the diacid dimer is derived from the dimerization of linoleic acid.

According to one embodiment, the diacid dimer may be in a product which also contains a trimeric acid and/or a monomeric acid, in proportions that depend on the degree of purity of the product. Products whose diacid dimer content may be greater than 70% and others whose diacid dimer content has been adjusted to 90% or more can be conventionally found commercially.

Polyols

The term "polyol" is intended to denote any hydrocarbon-based compound comprising at least two hydroxyl functions and preferably containing from 4 to 40 carbon atoms, or for example from 6 to 36 carbon atoms, or for example from 8 to 32 carbon atoms, or for example from 16 to 28 carbon atoms and for example from 18 to 24 carbon atoms, including all ranges and subranges therebetween. The hydrocarbon-based chains may be interrupted, where appropriate, by the presence of at least one heteroatom, and for example an oxygen atom. The polyol may be selected, for example, from the group consisting of a diol, a triol, a tetraol, or a pentaol, or an ester thereof.

A polyol or a polyol ester that is suitable for use in the present invention may comprise, for example, from 2 to 12 hydroxyl functions, or for example from 2 to 8 hydroxyl functions, or for example from 4 to 6 hydroxyl functions, including all ranges and subranges therebetween. Where appropriate, the hydroxyl functions, other than those already employed in an ester bond with the diacid dimer, may also be employed, wholly or partly in other ester bonds via reaction with acid molecules other than the diacid dimer.

The polyol or an ester thereof that is suitable for use in the present invention may be selected from the group consisting of linear, branched, cyclic or polycyclic, saturated or unsaturated alcohols. For example, the polyol may be a diol, or an ester thereof, selected for example from the group consisting of a fatty alcohol dimer, a monoglycerol or polyglycerol, a $C_{2-4}$ monoalkylene or polyalkylene glycol, 1,4-butanediol and pentaerythritol. As examples of diols that are also suitable for use in the invention, mention may be made, in a non-exhaustive manner, of butanediol, pentanediol, propanediol, hexanediol, hexylene glycol, heptanediol, octanediol, nonanediol, decanediol, 1-decanediol, dodecanediol, tridecanediol, tetradecanediol, pentadecanediol, hexadecanediol, nonadecanediol, octadecanediol, cyclohexanediol, diglycerol, erythritol, pentaerythritol, xylitol, sorbitol, ethylene glycol and xylene glycol, and isomers thereof.

According to certain embodiments of the present invention, diol dimers may be used as a suitable polyol. The term "diol dimer" is intended to mean saturated diols derived from the hydrogenation of the corresponding diacid dimers, a diacid dimer being as defined above, and for example a diacid dimer of at least one unsaturated fatty acid. A diol dimer may be, for example, dilinoleol. Another may be, for example, diglycerol, a glycerol dimer resulting from the condensation of two molecules of glycerol, with the loss of a water molecule. The term "diglycerol" denotes any isomer combination that can result from such a condensation, for instance linear isomers, branched isomers and, where appropriate, cyclic isomers resulting from an intramolecular dehydration of a diglycerol molecule.

As examples of acid molecules that can interact with one or more hydroxyl functions of the polyol, not engaged in the ester bond with the diacid dimer, mention may be made, in a non-limiting manner, of molecules derived from isostearic acid, behenic acid, phytosteric acid, stearic acid or cetylic acid.

An ester that is suitable for use in the present invention may be obtained by reacting a polyol or an ester thereof with a diacid dimer, in a molar ratio of about 1.0:0.2-1.0, including all ranges and subranges therebetween.

An ester used in the context of the present invention may be used in the form of a mixture of various esters. For example, an ester that may be suitable for use in the present invention may be obtained by reacting a dimerdilinoleic acid with a dilinoleol and, where appropriate, at least one additional monoalcohol selected for example from the group consisting of behenol, isostearol, phytosterol, stearol and cetol, and mixtures thereof.

An ester that is suitable for use in the invention may be obtained, for example, by reacting a glycerol, an isostearic acid and a dimerdilinoleic acid, for example in a molar ratio of 1.0:0.2-1.0:0.5-0.9, including all ranges and subranges therebetween.

As examples of esters of dimerdilinoleic acid and of polyol(s), or an ester thereof, suitable for the invention, mention may be made of the esters described in patent applications JP 2003-226609, JP 2004-256515 and JP 2005-179377, the entire contents of which are hereby incorporated by reference in their entirety.

According to certain embodiments of the present invention, an ester in accordance with the invention may comprise an alternating sequence of diacid dimer residue(s) and of residue(s) related to the said polyol(s), and for example to the said diol(s), the said polyols or diols being, for example, as defined above. Thus, for example, in such a configuration, each of the two ends of the said sequence may bear, respectively, a unit OR' and OR" with R' and R" representing, independently of each other, a hydrogen atom or OR' and OR" representing, independently of each other, a $C_2$ to $C_{36}$, for example $C_8$ to $C_{24}$, for example $C_{12}$ to $C_{20}$ and for example $C_{16}$ to $C_{18}$ hydrocarbon based monoalcohol residue.

An ester that is suitable for use in the invention may be selected from the group consisting of esters of general formula (I), (II) or (IV) described below, or a mixture thereof.

According to certain embodiments of the present invention, an ester of polyol(s) and of fatty diacid dimer, or an ester thereof, that may be suitable for use in the present invention may have the general formula (I) below:

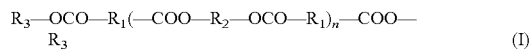

$$R_3-OCO-R_1(-COO-R_2-OCO-R_1)_n-COO-R_3 \qquad (I)$$

in which: $COR_1CO$ represents a fatty diacid dimer residue; $OR_2O$ represents a fatty alcohol dimer residue; $OR_3$ represents a hydrocarbon-based monoalcohol residue; and n is an integer ranging from 1 to 15, for example from 2 to 10 or for example from 5 to 7, including all ranges and subranges therebetween. According to one embodiment variant, $COR_1CO$ may represent a dimerdilinoleate residue. According to one embodiment variant, $OR_2O$ may represent a dimerdilinoleyl residue. Moreover, $OR_3$ may represent a hydrocarbon-based monoalcohol residue selected, for example, from the group consisting of behenyl, isostearyl and phytosteryl residues, and mixtures thereof.

According to certain embodiments of the present invention, the ester of dimerdilinoleic acid and of polyol(s) and of fatty diacid dimer, or an ester thereof, that may be suitable for use in the invention may for example have the general formula (II) below:

$$HO-R'_2(O-C-R'_1-CO-O-R'_2)_n-OH \qquad (II)$$

in which n is an integer ranging from 1 to 15, for example from 2 to 10 and in particular from 5 to 7, including all ranges and subranges therebetween; $COR'_1CO$ represents a fatty diacid dimer residue; $OR'_2O$ represents a diglyceryl residue of general formula (III) below:

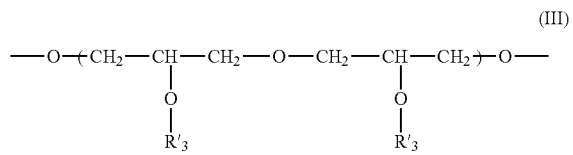

(III)

in which: $R'_3$ represents H or $OR'_3$ represents a fatty acid residue. According to one embodiment variant, $COR'_1CO$ may represent a dimerdilinoleate residue. According to one embodiment variant, the fatty acid residue featured by $OR'_3$ may be an isostearyl residue.

According to certain embodiments of the present invention, an ester of dimerdilinoleic acid and of polyol(s) and of fatty diacid dimer, or an ester thereof, which may be suitable for use in the present invention, may be of formula (IV) below:

$$HO-R_1''-(-OCO-R_2''-COO-R_1''-)_h-OH \qquad (IV)$$

in which $OR_1''O$ represents a diol dimer residue obtained by hydrogenation of a dimerdilinoleic acid; $COR_2''CO$ represents a fatty diacid dimer residue; and h represents an integer ranging from 1 to 9, for example from 2 to 8 and for example from 4 to 6, including all ranges and subranges therebetween. According to one embodiment, $COR_2''CO$ may represent a dimerdilinoleate residue.

An ester that is suitable for the invention may be selected for example from group consisting of the esters having the following INCI nomenclature: polyglyceryl-2 isostearate dimerdilinoleate copolymer, bis-behenyl/isostearyl/phytosteryl dimer dilinoleate, and mixtures thereof. Such compounds may be obtained, for example, under the reference Hailuscent ISDA (Kokyu Alcohol) and Plandool-G, Lusplan DD-DA5, Lusplan DD-DA7, PHY/IS-DA and Lusplan DD-DAS (Nippon Fine Chemical Company Ltd). For example, Lusplan DD-DA5 and Lusplan DD-DA7 are described in patent application FR 03/02809, the entire contents of which is hereby incorporated by reference.

In the composition of the present invention, the ester(s) of polyol and of fatty diacid dimer (or an ester thereof) is/are preferably present in an amount of from about 0.1 to about 60 percent by weight, more preferably from 1 to 40 percent by weight, more preferably from 1 to 20 percent by weight and most preferably from 1 to 10 percent by weight of the total weight of the composition, including all ranges and subranges therebetween.

According to preferred embodiments, the tackifier/acrylic film forming agent and the ester(s) of polyol and of fatty diacid dimer (or an ester thereof) are present in the compositions of the present invention in a combined weight ratio of between 10:1 and 1:10, preferably between 7:1 and 1:7, and preferably between 4:1 and 1:4, including all ranges and subranges therebetween.

Oil Phase

According to the present invention, compositions comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the composition of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers.

Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to certain embodiments of the present invention, the compositions of the present invention comprise at least one silicone oil. Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenyldimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

According to preferred embodiments, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to particularly preferred embodiments, the compositions of the present invention, at least one volatile oil and at least one non-volatile oil are present. In accordance with these preferred embodiments, the at least one volatile oil is present in the compositions of the present invention in an amount ranging from about 5 to about 50% by weight, preferably from about 10 to about 40% by weight, and preferably from about 12 to about 37% by weight, based on the total weight of the composition, including all ranges and subranges within these ranges, and the at least one non-volatile oil is present in the compositions of the present invention in an amount ranging from about 10 to about 50% by weight, preferably from about 12 to about 45% by weight, and preferably from about 15 to about 40% by weight, based on the total weight of the composition, including all ranges and subranges within these ranges.

According to preferred embodiments of the present invention, the compositions of the present invention comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.; silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; silicone resin waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

If present, the wax or waxes may be present in an amount ranging from 0.1 to 50% by weight relative to the total weight of the composition, for example from 1 to 30%, and for example from 3 to 25%, including all ranges and subranges therebetween.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin and lips by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag, spreadability, and/or reduced tackiness), improved shine (initial shine after application and shine 1 hour after application), increased anti-smudging properties, increased stability and/or increased long wear properties are provided.

According to other embodiments of the present invention, methods of improving the stability, anti-smudging, transfer-resistance, adherence, shine (initial shine after application and shine 1 hour after application) and/or long wear properties of a composition, comprising adding at least one silicon resin comprising at least one T unit and at least one tackifier are provided.

According to further embodiments of the present invention, methods of improving the feel or texture of a composition, preferably a makeup compositions such as a foundation or lip composition, comprising adding at least one silicon resin comprising at least one T unit and at least one tackifier are provided Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The following compositions were prepared:

Example 1

Lipstick

| | |
|---|---|
| Regalite | 8% |
| isohexadecane | 21.57% |
| hydrogenated polyisobutene | 1.8% |
| octyldodecyl neopentanoate | 4.8% |
| bis-behenyl/isostearyl/phytosteryl dimer dilinoleate | 5.15% |
| Vp/hexadecene copolymer | 6.6% |
| polyethylene | 5.5% |
| polyethylene | 5.5% |
| VP/eicosane copolymer | 1% |
| polyglycerol 3 beeswax | 1.7% |
| Acrylic acid/isobutyl acrylate/isobornyl acrylate copolymer | 8% |
| pigment | 5.66% |
| HDI/trimethylol hexylactone | 1% |
| pearl | 4.94% |
| trimethylsiloxyphenyl dimethicone | 18.79% |

Example 2

Lipstick

| Phase | INCIUS | % |
|---|---|---|
| A | HYDROGENATED POLYISOBUTENE | 0.63 |
| A | OCTYLDODECYL NEOPENTANOATE | 1.68 |
| A | PIGMENTS | 2.89 |
| A | BIS-BEHENYL/ISOSTEARYL/PHYTOSTERYL DIMER DILINOLEYL DIMER DILINOLEATE | 1.03 |
| B | HYDROGENATED POLYISOBUTENE | 2.47 |
| B | VP/HEXADECENE COPOLYMER | 6.60 |
| B | OCTYLDODECYL NEOPENTANOATE | 3.12 |
| B | REGALITE | 8.00 |
| B | Synamer 3 | 8.00 |
| B | ISOHEXADECANE | 21.57 |
| B | BIS-BEHENYL/ISOSTEARYL/PHYTOSTERYL DIMER DILINOLEYL DIMER DILINOLEATE | 4.12 |
| C | VP/EICOSENE COPOLYMER | 1.00 |
| C | polyglycerol 3 beeswax | 1.70 |
| C | POLYETHYLENE 400/500 | 11.00 |
| | wax total | 13.70 |
| D | Filler (dry total) | 8.0 |
| E | TRIMETHYLSILOXYPHENYL DIMETHICONE | 18.79 |
| | TOTAL | 100.00 |

Procedure for Making Example 2.

In a Fondue kettle, wet pigment in oil mixture (phase A) was mixed moderately, and roller milled until pigment was well dispersed.

(Phase B) Hydrogenated polyisobutene, VP/Hexadecene copolymer, octyldodecyl neopentanoate and bis-benenyl/isostearyl/phytosteryl dimer dilinoleyl dimer dilinoleate were heated up to 90 C with 320 rpm mixing. Regalite was dispersed little by little at 400 rpm until the solution became clear (approximately 1 hour). Synamer 3 was added and mixed well with 500 rpm (approximately 10 minutes).

Heating was stopped and the temperature was reduced to 60 C. Isohexadecane was added and mixed well at 500 rpm (approximately 20 minutes).

(Phase C) The wax mixture was melted in the main kettle. Color Grind (Phase A) was added to the wax and mixed at 400 rpm. To this mixture, Phase B was added and mixed at 500 rpm until uniform.

Filler (Phase D) was added and dispersed using cowles blade at 500 rpm (approximately 30 minutes).

Phase E (trimethylsiloxyphenyl dimethicone) was added and mixed at 650 rpm, then at 380 rpm.

The resulting mixture was poured at 95 C into a mold which had been pre-heated to 42 C (no silicon spray coating). Then, it was chilled for 30 minutes.

Example 3

Comparative Testing

A composition containing Plandool G (bis-behenyl/isostearyl/phytosteryl dimer dilinoleyl dimer dilinoleate), Synamer 3 (acrylic acid/isobutyl acrylate/isobornyl acrylate copolymer), Regalite (hydrogenated styrene/methyl styrene/indene copolymer), and isohexadecane along with other ingredients was prepared. The composition showed a classic wear score 58+/−10, 1 hr migration 0.0+/−0.0, immediate shine 128.3+/−9.9 and 1 hr shine 120.5+/−10.8.

A similar composition containing Synamer 3, Regalite, isohexadecane, but no Plandool G was prepared. This composition showed inferior scores, particularly with respect to lasting shine—a classic wear score 56+/−9, 1 hr migration 0.0+/−0.0, immediate shine 131.0+/−14.9 and 1 hr shine 108.3+/−10.9.

This comparison illustrates that by introducing the ester compound such as plandool G into a long wear formulation containing acrylic polymer and styrene polymer, overtime shine improved while maintaining wear of color.

Also, a composition containing Plandool G, Synamer 3, Regalite and isohexadecane showed initial "greasiness" of the lipstick 10.8 out of 15 and 2 hr "greasiness" 3 out of 15. On the other hand, a composition containing Synamer 3, Regalite, and isohexadecane, but no Plandool G showed initial "greasiness" of lipstick 7.7 out of 15 and 2 hr "greasiness" 2 out of 15. This comparison illustrates that by introducing ester compound such as plandool G into a long wear formulation containing acrylic polymer and styrene polymer, initial and overtime comfort/moisture feel improved while maintaining wear of color.

What is claimed is:

1. A composition, consisting of
   at least one ester of polyol(s) and of fatty diacid dimer or an ester thereof in an amount of 1 to 40% by weight relative to the total weight of the composition and selected from the group consisting of polyglyceryl-2 isostearate dimerdilinoleate copolymer, bis-behenyl/isostearyl/phytosteryl dimer dilinoleate and a mixture thereof,
   a film forming copolymer of acrylic acid, isobutyl acrylate and isobornyl acetate in an amount of 0.1 to 30% by weight relative to the total weight of the composition,
   a volatile oil,
   at least two polyethylene waxes in a weight ratio of 1:1,
   a hydrogenated styrene/methyl styrene/indene copolymer tackifier in an amount of 0.1 to about 30% by weight relative to the total weight of the composition,
   optionally at least one colorant,
   optionally at least one volatile oil, and
   optionally at least one additional wax,
   wherein the composition is in the form of a lipstick.

2. The composition of claim 1, wherein the at least one coloring agent is present in the composition.

3. The composition of claim 1, wherein the composition is anhydrous.

4. The composition of claim 1, wherein the at least one additional wax is present.

5. The composition of claim 4, wherein the wax is a silicone resin wax.

6. A method of making up lips comprising applying the composition of claim 1 to the lips.

7. A method of making up skin comprising applying the composition of claim 1 to the skin.

8. The composition of claim 1, wherein the film forming copolymer is present in an amount of from 1 to 20% by weight of the total weight of the composition.

9. The composition of claim 1, wherein the film forming copolymer is present in an amount of from 5 to 15% by weight of the total weight of the composition.

10. The composition of claim 1, wherein the hydrogenated styrene/methyl styrene/indene copolymer tackifier is present in an amount of 3 to about 20% by weight relative to the total weight of the composition.

11. The composition of claim 1, wherein the hydrogenated styrene/methyl styrene/indene copolymer tackifier is present in an amount of 5 to about 15% by weight relative to the total weight of the composition.

12. The composition of claim 1, wherein the at least one ester of polyol(s) and of fatty diacid dimer or an ester thereof is present in an amount of 1 to 20% by weight relative to the total weight of the composition.

13. The composition of claim 1, wherein the at least one ester of polyol(s) and of fatty diacid dimer or an ester thereof is present in an amount of 1 to 10% by weight relative to the total weight of the composition.

14. The composition of claim 1, wherein the at least one non-volatile oil is present and is selected from the group consisting of trimethylsiloxyphenyl dimethicone, and octyldodecyl neopentanoate.

* * * * *

UNITED STATES PATENT AND TRADEMARK OFFICE
CERTIFICATE OF CORRECTION

PATENT NO.      : 9,226,888 B2  
APPLICATION NO. : 14/354719  
DATED           : January 5, 2016  
INVENTOR(S)     : Yoriko Bukawa et al.

Page 1 of 1

It is certified that error appears in the above-identified patent and that said Letters Patent is hereby corrected as shown below:

Title Page [75] Inventors: "Yoriko Bukawa, Chuou-ku (JP);"

should read

--Yoriko Bukawa, Chuo-ku, Tokyo (JP)--.

Signed and Sealed this  
Nineteenth Day of July, 2016

Michelle K. Lee  
*Director of the United States Patent and Trademark Office*